United States Patent [19]

Harding et al.

[11] Patent Number: 4,516,261
[45] Date of Patent: May 7, 1985

[54] DEVICE FOR REDUCING FAULTS IN LAYER IMAGES OF A THREE-DIMENSIONAL OBJECT FORMED BY MEANS OF PENETRATING RADIATION

[75] Inventors: Geoffrey Harding, Rellingen; Erhard Klotz, Halstenbek, both of Fed. Rep. of Germany

[73] Assignee: U.S. Philips Corporation, New York, N.Y.

[21] Appl. No.: 203,163

[22] Filed: Nov. 3, 1980

[30] Foreign Application Priority Data

Nov. 8, 1979 [DE] Fed. Rep. of Germany ....... 2945057

[51] Int. Cl.³ .............................................. G06K 9/00
[52] U.S. Cl. ........................................ 382/6; 364/414; 378/25; 378/901; 382/54; 382/56
[58] Field of Search ...................... 364/414; 382/6, 56, 382/54; 378/25, 4, 9, 11, 15, 21, 22, 24, 26, 210, 901

[56] References Cited

U.S. PATENT DOCUMENTS

| | | | |
|---|---|---|---|
| 3,984,693 | 10/1976 | Tomita et al. | 378/25 |
| 4,078,177 | 7/1978 | Tiemens | 250/323 |
| 4,118,099 | 9/1978 | Weiss et al. | 350/373 |
| 4,217,641 | 8/1980 | Naparstek | 382/6 |
| 4,223,384 | 9/1980 | Hounsfield et al. | 378/901 |
| 4,233,662 | 11/1980 | Le May | 378/901 |
| 4,298,944 | 11/1981 | Stoub et al. | 382/6 |
| 4,322,808 | 3/1982 | Weiss | 382/56 |
| 4,323,973 | 4/1982 | Greenfield | 382/6 |
| 4,335,427 | 6/1982 | Hunt et al. | 382/6 |

FOREIGN PATENT DOCUMENTS

| | | |
|---|---|---|
| 2517268 | 10/1976 | Fed. Rep. of Germany . |
| 2722141 | 12/1978 | Fed. Rep. of Germany . |
| 2746035 | 4/1979 | Fed. Rep. of Germany . |
| 2016855 | 9/1979 | United Kingdom . |

Primary Examiner—Leo H. Boudreau
Attorney, Agent, or Firm—Marc D. Schechter

[57] ABSTRACT

A device for reducing artefacts in layer images. Several layer images are formed of an object layer by irradiation from different directions. The same points of these layer images are compared in order to obtain a corrected layer image: when corresponding image information is present in all image points compared, the image information is transferred to corresponding layer image points in a corrected layer image; when the image information in the compared image points is not the same, that information is at least partly suppressed.

12 Claims, 12 Drawing Figures

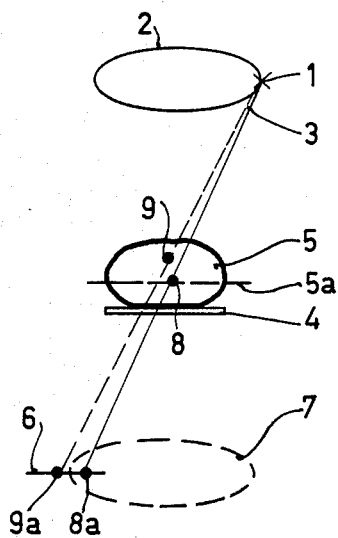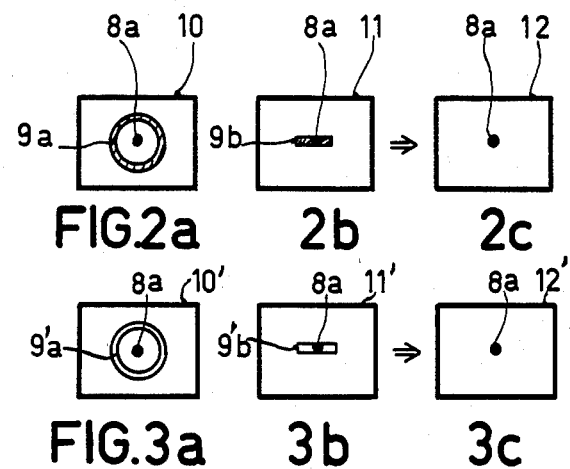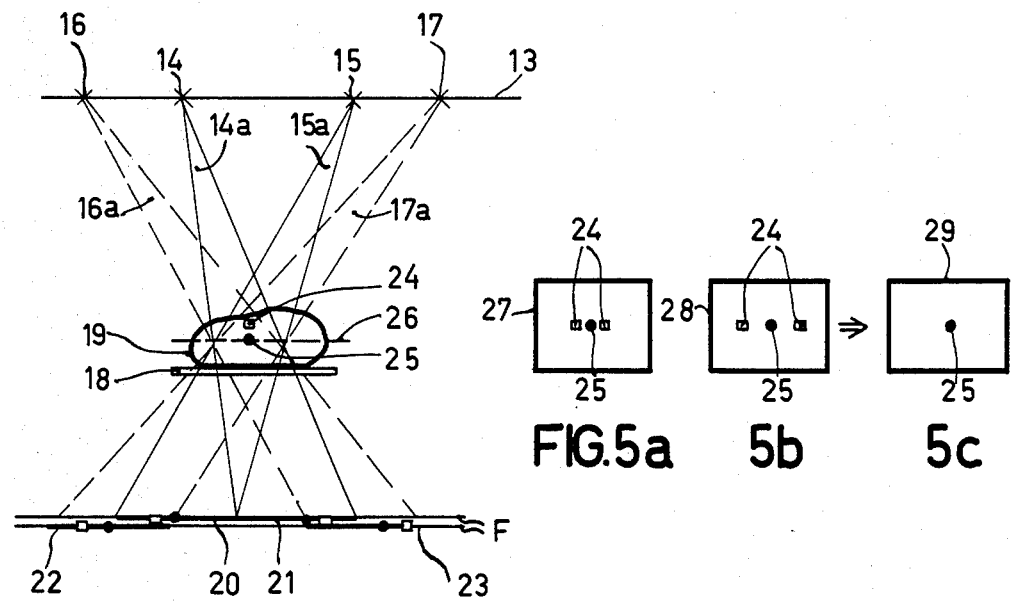

DEVICE FOR REDUCING FAULTS IN LAYER IMAGES OF A THREE-DIMENSIONAL OBJECT FORMED BY MEANS OF PENETRATING RADIATION

BACKGROUND OF THE INVENTION

The invention relates to a device for reducing distortions in layer images of a three-dimensional object formed by means of penetrating radiation.

From German Offenlegungsschrift No. 28 10 608 it is known to record individual perspective images either separately or as a superposition image and to displace and superpose these images in a suitable manner in order to form layer images. In order to reduce artefacts in the reconstructed layer image, corresponding points of the perspective images are examined in order to determine whether they belong to the selected layer, in which case they have to be displayed as common layer image points, or whether they do not belong thereto, in which case they are ignored for the imaging. Prior to the mutual comparison, the perspective images can also be filtered, so that the low spatial frequency components are attenuated (see Joseph W. Goodman, "Fourier Optics", McGraw-Hill, 1968, page 147, second paragraph).

The known method, where the absolute gray values are derived from corresponding points in the perspective images recorded by means of only one group of radiation source positions, offers better results as the contrast of the perspective images is higher. This method, therefore, is suitable mainly for angiographic examinations where the object structures to be examined are accentuated by means of a contrast medium. It is assumed that several of such object structures are not superposed in the perspective images, because otherwise the contrast would be less.

SUMMARY OF THE INVENTION

It is an object of the invention to provide a device in which the faults in layer images of a three-dimensional object are reduced.

This object is achieved in accordance with the invention in that a device of the described kind comprises means for forming layer images of one and the same object layer by irradiation from different directions, an analyzer for analyzing the information of points of the various layer images, and a device for correcting the ultimate image of the object layer by the addition of information of points of the various layer images which contain corresponding information, and by at least partly suppressing the information of points containing noncorresponding information.

Thus, in the device in accordance with the invention, first a set of layer images (tomograms) is formed of one and the same layer of an object by irradiation from different directions. Further object layers, situated underneath or above the selected object layer, however, are also included in the relevant layer images, be it in a blurred manner, so that image distortions would be produced. However, because of the fact that a different radiation geometry is used for each layer image, the images of the selected object layer exhibit different "blurs". By comparison of the image information present in corresponding points in the relevant layer images, the blurs can be suppressed; image information appearing in corresponding image points is transferred to a corresponding location in a corrected layer image, while noncorresponding image information is suppressed. The separate layer images are displayed with the same brightness or density.

The layer images can be formed by means of various methods. For example, they can be formed by means of tomography, where a radiation source and a detector are moved along given, associated paths. Layer images (blurring patterns) of a single object layer are thus formed along different paths, and recorded. The blurring patterns at the same time represent a perspective image group.

Layer images can also be obtained by means of pulse tomosynthesis, where the object is irradiated from a large number of radiation source positions which are situated in one plane. For example, the object can be successively irradiated from different groups of radiation source positions in order to obtain perspective image groups wherefrom layer images can be reconstructed with different radiation geometries for an object layer.

It is alternatively possible to irradiate the object by means of a large number of radiation sources which are situated in one radiation source plane so that each time all perspective images are recorded in mutually parallel planes which are situated at different distances from the object (see also German Patent Application No. P 25 14 988). A layer image is obtained from the perspective images of one plane; the layer images are adapted to each other as regards scale and are subsequently compared.

Layer images with different radiation geometry can also be obtained by the combined imaging of a superposition image which consists of different perspective images obtained, with different groups of imaging elements of an imaging matrix, for example, a lens matrix. The distribution of the imaging elements thus corresponds to the flat distribution of the radiation source positions. With this method, variation of the scale of the layer images prior to comparison can be dispensed with.

According to the prior art methods, the individual perspective images of the relevant perspective image groups can thus also be compared after suitable shifting in the corresponding image points, so that the superposition produces layer images which contain less artefacts.

The proposed device is not restricted to images obtained by means of radiation sources arranged outside the object. The device also concerns images which are generated by radiation sources present within the body like, for example, an administered radioactive sample in nuclear medicine.

In order to obtain the corrected layer images in a preferred embodiment of the invention the gray values at the relevant points of the layer images are compared, so that artefact-poor layer images are simply obtained.

In order to obtain the corrected layer images in a further preferred embodiment in accordance with the invention, direction-dependent changes of the gray values are determined and compared in the relevant layer images. By determination of the second deviative of the value variations, (for example, of the image density in a given direction), contour images can be obtained which mark the contours of the object structures. Contour images of this kind do not contain gray tone information, but therefrom extremely artefact-poor corrected layer images which correspond to the so-called Xerotomograms can be obtained by the described point-wise comparison. Obviously, a layer image can be superposed on or added to such corrected layer images.

BRIEF DESCRIPTION OF THE DRAWING

FIG. 1 shows a tomography apparatus comprising a moving radiation source and recording layer.

FIGS. 2a–c show two layer images, realized in different ways and representing the same object layer, and a corrected layer image formed therefrom.

FIGS. 3a–c show two contour images obtained from the layer images and a corrected layer image obtained therefrom.

FIG. 4 shows a pulse tomosynthesis apparatus.

FIGS. 5a–c show two layer images of the same object layer obtained thereby in different ways, and the corrected layer image obtained therefrom.

DESCRIPTION OF THE PREFERRED EMBODIMENTS

Figure 6:
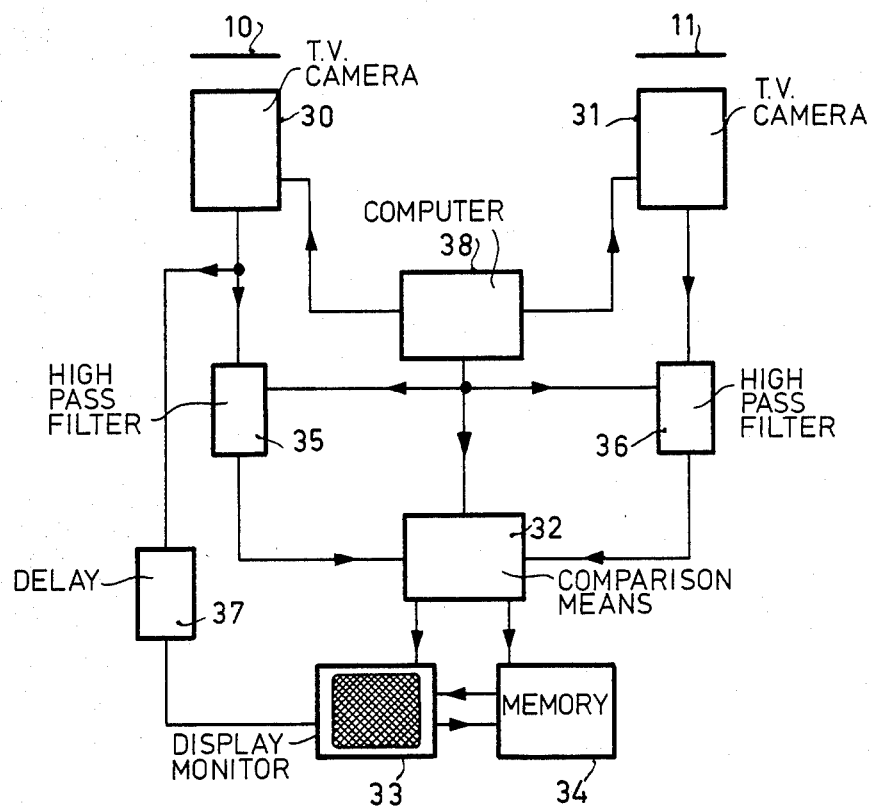
FIG. 6 shows an electronic device for the point-wise comparison of layer images or perspective images.

FIG. 1 diagrammatically shows a conventional tomography apparatus. AN X-ray tube 1 is moved along, for example, a flat, circular path 2. The X-ray tube, by way of a suitably stopped radiation beam 3, irradiates an object 5, for example, an organ of a human body which is positioned on an table 4. Underneath the table a movable record carrier 6 is arranged, for example, an X-ray film, which is exposed to the radiation beam 3 and which is situated in a plane parallel to the radiation source plane. The movements of the X-ray source 1 and the record carrier 6 are coupled, so that the record carrier also describes a circular path 7. When the X-ray tube 1 (which sharply images a given object layer 5a) is, for example, continuously activated on its path 2, a sharp image 8a of the object detail 8 situated within the object plane 5a is formed on the record carrier 6, while the object detail 9 which is situated above the object plane 5a is imaged on the record carrier 6 as a circular blurred image 9a. Thus, a layer image containing artefacts is formed thereon. The record carrier 6 may alternatively be the entrance screen of an X-ray image intensifier, so that the relevant perspective images can be electronically stored or superposed.

FIG. 2a shows such a layer image 10 with the object details 8a and 9a, the object detail 9a representing an artefact in the layer image 10, because this object detail 9 is not situated within the selected object layer 5a.

In order to eliminate this artefact, a further layer image 11 is formed from the same object layer 5a. However, in order to form the image 11 the X-ray tube 1 and the record carrier 6 follow a path other than the first path, (for example, a straight line). Consequently, the object detail 8 which is situated in the plane 5a is sharply imaged in the layer image 11, while the object detail 9 is blurred as a strip 9b. If corresponding points in the two layer images 10 and 11 are scanned a relatively artefact free corrected layer image 12 can be obtained; when the image information in the two compared image points is the same, information is taken over in the corresponding location in the corrected layer image 12, while image information in the points compared which does not correspond is completely or partly suppressed in the corrected layer image 12.

The gray values in the various image points can be considered as image information. The individual layer images 10 and 11, however, can also be filtered by means of a high-pass filter in order to attenuate low spatial frequency components. The gray value variations in the layer images 10 and 11 are thus measured and further layer images 10' and 11' as shown in the FIGS. 3a–c are formed which represent only the contours 9a', 9b of the object details 9a, b (so-termed contour images). These contour images can also be scanned or compared in the described manner in order to obtain a corrected layer image 12'. To this end, the contour images are, for example, electronically scanned line-by-line in order to determine the sign, the magnitude and the position of the variations of the gray values. Electronic comparison of these values of two contour images can thus produce a corrected layer image. The artefacts can thus be further reduced. The high-pass filtering of the layer images 10, 11 can be electronically or optically performed, for example, by means of coherent or incoherent light.

Obviously, the X-ray tube 1 and the record carrier 6 can alternatively be moved along other suitable paths which are different for the relevant layer images. Moreover, according to this method more than two layer images can be formed and compared in order to obtain a corrected layer image.

The proposed method is not restricted to layer images produced by means of the described tomography apparatus, but in general applies to layer images obtained in an arbitrary manner.

FIG. 4 shows a pulse tomosynthesis apparatus by way of example. This apparatus comprises two groups of X-ray tubes 14, 15 and 16, 17 which are situated in a radiation source plane 13 and which irradiate a common stopped zone of an object 19 on an object table 18 by way of their radiation beams 14a, 15a, 16a, 17a. Each of the illustration groups comprises only two X-rays tubes. In practice a large number of X-ray tubes, for example from 20 to 60, is used in each group. These groups are successively flashed. Perspective image groups 20, 21 and 22, 23 containing the object details 24, 25 are thus recorded on separate films F in a plane parallel to the radiation source plane 1 (for the sake of clarity, FIG. 4 shows two planes). The perspective images of a group may be separately recorded on a film or may be recorded in a superposed manner. Layer images of the object 19 can be reconstructed from the perspective image groups 20, 21, and 22, 23 by means of known methods (for example, see German Offenlegungsschrift No. 27 46 035).

FIG. 5a shows such a layer image 27 which represents an object plane 26 in FIG. 4. This image was reconstructed from the perspective images 20 and 21. It contains the object detail 25 as well as the object detail 24 which appears twice at a given distance therefrom and which represents a fault in the layer image 27.

The layer image 28 in FIG. 5b, reconstructed from the perspective images 22 and 23 and also representing the desired object layer 26, also contains the object details 24 and 25. However, in comparison with FIG. 5a the object details 24 and 25 are situated at a different distance from each other, so that a corrected layer image 29 can be obtained (FIG. 5c) in the described manner by point-wise comparison of the image information of the layer images 27 and 28.

However, the X-ray tubes 14 to 17 of the device shown in FIG. 4 can also be simultaneously flashed (multiple radiation source). In this case, for example, each time four perspective images in several parallel planes which are situated at a different distance from the object are recorded. From the perspective images of each plane, layer images are formed which have to be brought to the same scale with respect to each other before they can be compared. For example, the perspective images in the different planes can be simultaneously recorded by means of a simultaneous cassette.

The comparison of the individual layer images can be performed electronically in the described manner by scanning the layer images line-by-line. The comparison of the gray values in the relevant image points is then performed, for example, by comparison of two signal voltages, each of which is associated with one of the image points to be compared.

In order to form corrected layer images (for example, contour images which represent the same object layer and which contain only gray value variations recorded on a film with high contrast), the images thus obtained are superposed and recorded again on a film with high contrast (see Joseph W. Goodman, "Fourier Optics", McGraw-Hill, 1968, page 152).

FIG. 6 shows an electronic device for the point-by-point comparison of layer images or perspective images. The references 10 and 11 denote the layer images shown in the FIGS. 2a and 2b, respectively. These images are scanned line-by-line by means of electronic cameras 30, and 31. If only the gray values at corresponding image points of the layer images 10, 11 are to be compared, the image signals obtained are applied directly to a comparison unit 32 in order to determine a corrected layer image which can be displayed on a monitor 33 or which can be stored in the memory 34. To this end, the high-pass filters 35 and 36 are internally bridged. If contour images have to be made from the layer images 10 and 11, the output signals of the cameras 30 and 31 are applied to the comparison unit 32 or the monitor 33 or the memory 34 via high-pass filters 35 and 36. The scanning of the layer images can also be performed in different directions for the complete recording of all contours. If an original layer image, for example, 10 is to be superposed on the corrected layer image, the output signal of the camera 30 can be applied directly, via a delay member 37, to the monitor 33 or the memory 34 in a suitable manner. The various operations are then controlled by a computer 38.

Obviously, the apparatus shown in FIG. 6 is also suitable for comparison of separate contour images optically obtained from the layer images 10 and 11. The contour images are then arranged in the positions of the layer images 10 and 11, and the high-pass filters 35 and 36 are internally bridged.

This apparatus is also suitable for point-by-point comparison of separate perspective images in order to obtain artefact-free layer images. However, the perspective images must be suitably shifted with respect to each other for the reproduction of a given object layer; this can be realized by suitable control of the cameras 30 and 31 by means of the computer 38. The addition to or superposition of the perspective images on a layer image takes place in comparison unit 32. This image is applied, for example, to the monitor 33. The points of the perspective images which correspond in the layer images are at the same time examined in the comparison unit 32 to determine whether they contain corresponding image information. In that case they are taken over in the corrected layer image. If they contain noncorresponding image information, they are suppressed. Furthermore, from the perspective images perspective contour images can be obtained, prior to the superposition. The contour images are superposed in the described manner in order to form a contour layer image. This contour layer image, of course, can also be added to a perspective image.

The comparison of the layer images or perspective images need not be restricted to two images at a time, but can also be performed for more than two images.

What is claimed is:

1. A method of reducing distortions in layer images comprising the steps of:
    forming at least first and second groups of perspective images of the object, each perspective image being formed by irradiating the object from a given direction, the irradiation directions which correspond to perspective images in the first group being different from the irradiation directions which correspond to perspective images in the second group;
    forming at least first and second layer images of a single object layer, said first layer image being formed by superimposing the first group of perspective images, said second layer image being formed by superimposing the second group of perspective images;
    analyzing information at corresponding points in the two layer images to determine whether or not those points contain corresponding information; and
    forming an ultimate corrected image of the object layer by the carrying over of information from points in the layer images which contain corresponding information and by at least partially supressing information from such points which do not contain corresponding information.

2. A method as claimed in claim 1, characterized in that the step of forming the ultimate corrected image of the object layer comprises the step of adding information from points in the various layer images which contain corresponding information.

3. A device for reducing distortions in layer images of a three-dimensional object, said device comprising:
    means for forming at least first and second groups of perspective images of the object, each perspective image being formed by irradiating the object from a given direction, the irradiation directions which correspond to perspective images in the first group being different from the irradiation directions which correspond to perspective images in the second group;
    means for forming at least first and second layer images of a single object layer, said first layer image being formed by superimposing the first group of perspective images, said second layer image being formed by superimposing the second group of perspective images;
    means for analyzing information at corresponding points in the layer images to determine whether or not those points contain corresponding information; and
    means for forming an ultimate corrected image of the object layer by adding information from points in the various layer images which contain corresponding information and by at least partially supressing information from such points which do not contain corresponding information.

4. A device is claimed in claim 3, wherein the means for forming layer images comprise means for irradiating the three-dimensional object from a first group of radiation source positions which are situated in a radiation source plane to record a first perspective image group and for subsequently irradiating the object from at least one further group of radiation source positions which are situated in the radiation source plane and which differ at least partially from the first group in order to record at least one further perspective image group, and for reconstructing the layer images from said image groups.

5. A device as claimed in any one of the preceding claims, wherein the means for analyzing compare gray values at corresponding points in the layer images.

6. A device as claimed in claim 5, wherein the means for analyzing further includes means for discriminating direction dependent variations of the gray values in the layer images.

7. A device as claimed in claim 6, wherein the means for analyzing are an electronic circuit.

8. A device as claimed in claim 7, wherein the means for analyzing comprise a high-pass filter.

9. A device as claimed in claim 3 wherein the layer images are obtained with different radiation geometries and contain only gray value variations, further comprising high contrast film for recording the layer images and the superposition thereof.

10. A device as claimed in claim 3 further comprising means for superposing a directly formed layer image with the ultimate corrected image.

11. A device claimed in claim 3, further comprising separate television cameras for scanning each of the layer images; separate high-pass filters connected to outputs of each camera and including means for internally bridging the high-pass filters to disable the same, outputs of the high-pass filters being connected to inputs of a comparison means; and a monitor connected to the output of the comparison means for display or storage of the images.

12. A device claimed in claim 11, further comprising delay means connected to an output of at least one camera, an output of the delay means being connected to the monitor.

* * * * *